(12) United States Patent
Andersin

(10) Patent No.: US 7,370,560 B2
(45) Date of Patent: May 13, 2008

(54) RATCHET WRENCH

(75) Inventor: Per Andersin, Mölnlycke (SE)

(73) Assignee: Astra Tech AB, Molndal (SE)

( * ) Notice: Subject to any disclaimer, the term of this patent is extended or adjusted under 35 U.S.C. 154(b) by 0 days.

(21) Appl. No.: 11/724,264

(22) Filed: Mar. 15, 2007

(65) Prior Publication Data

US 2007/0214914 A1    Sep. 20, 2007

(30) Foreign Application Priority Data

Mar. 17, 2006    (EP) .................................. 06111341

(51) Int. Cl.
*B25B 13/46* (2006.01)
(52) U.S. Cl. .......................................... 81/58.5; 81/60
(58) Field of Classification Search ................ 81/58, 81/58.4, 58.5, 124.3, 124.7
See application file for complete search history.

(56) References Cited

U.S. PATENT DOCUMENTS 1,425,816 A    8/1922    Van Horn 4,913,009 A    4/1990    Andersen-Vie
2002/0170393 A1    11/2002    Yuan-Chin et al.
2005/0268751 A1    12/2005    Buchanan

FOREIGN PATENT DOCUMENTS

CH    19 245 A    6/1900
GB    250127 A    4/1926

*Primary Examiner*—David B Thomas
(74) *Attorney, Agent, or Firm*—Birch, Stewart, Kolasch & Birch, LLP

(57) ABSTRACT

The present invention discloses a ratchet wrench comprising a head (1) having a driving aperture (2) for engaging a drive means (4) rotatable therein. A handle (3) mounted for tilting movement in relation to said head (1), providing a first state where the drive means (4) is allowed to freely rotate and a second state where said drive means is engaged by said ratchet wrench for driving of the drive means. Said handle (3) is movable, into and out from a mounting position in the longitudinally direction of the handle (3). One end of said handle (3) is moveable through a first aperture (6) and further through a second aperture (7) of the head (1), said first and second apertures (6, 7) extending laterally relative the longitudinal axis of the driving aperture (2).

20 Claims, 4 Drawing Sheets

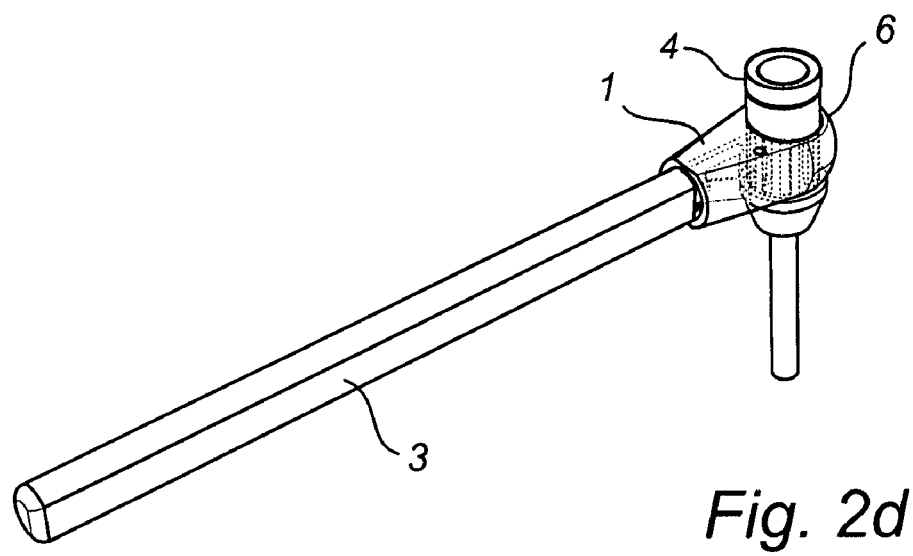
*Fig. 2d*
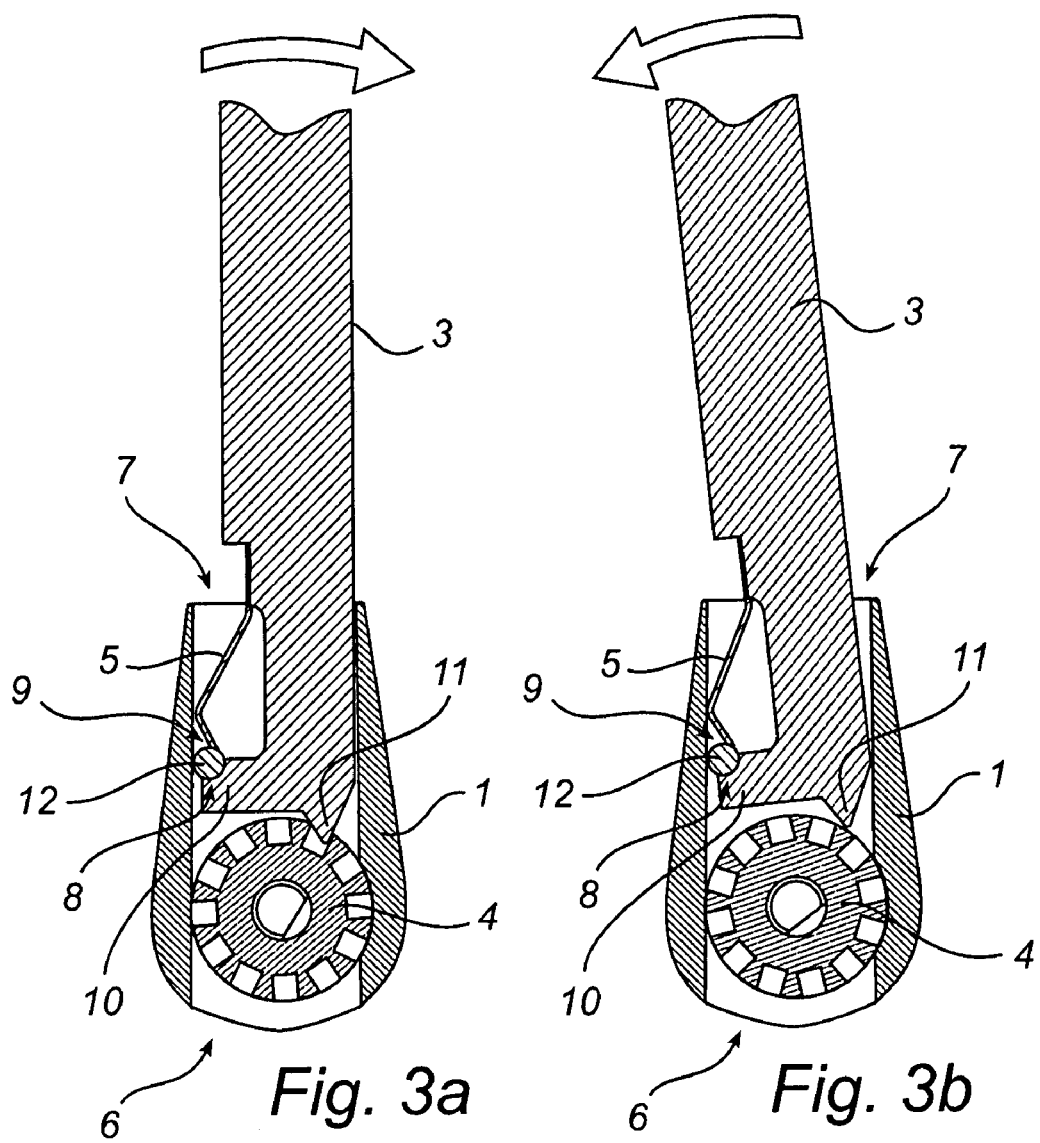
*Fig. 3a*  *Fig. 3b*

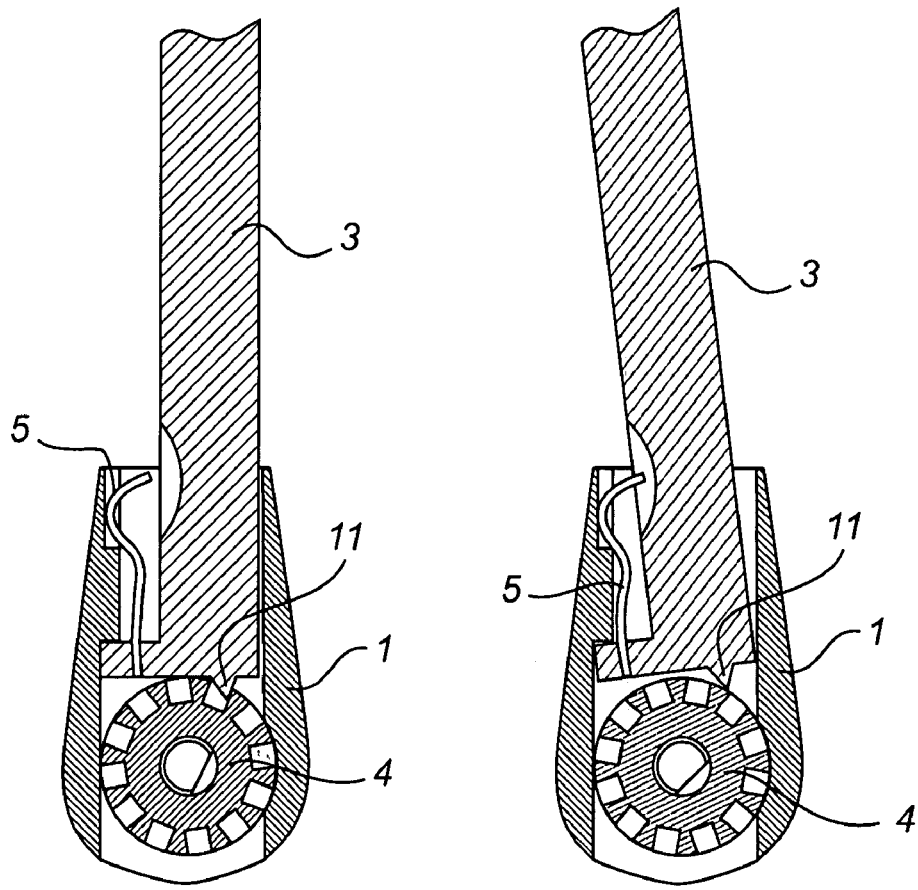
Fig. 4a   Fig. 4b
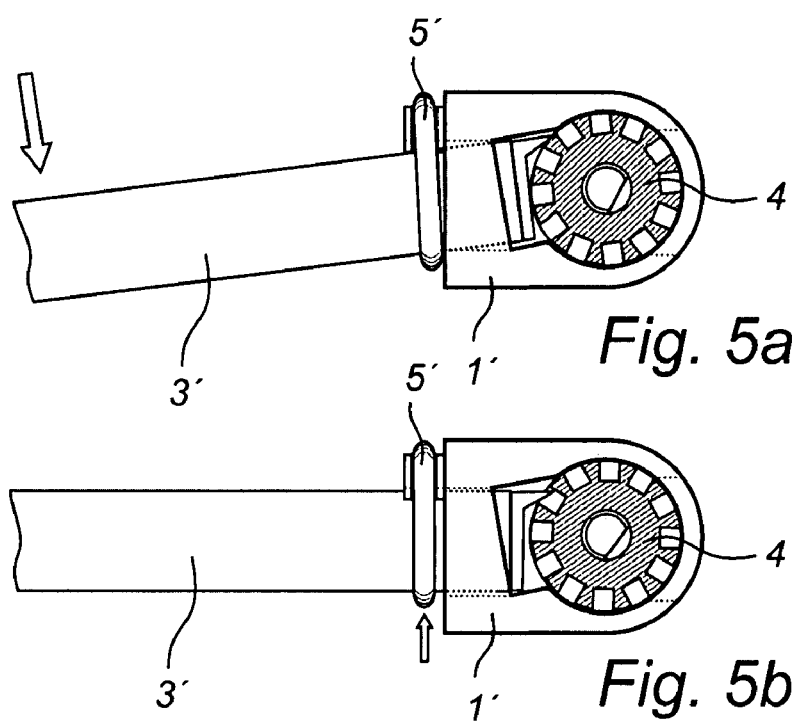
Fig. 5a
Fig. 5b

RATCHET WRENCH

FIELD OF THE INVENTION

The present invention relates to a ratchet wrench comprising a head having a driving aperture for engaging a drive means rotatable therein, a handle mounted for tilting movement in relation to said head. Hence a first state is provided where the drive means is allowed to freely rotate and a second state where said drive means is engaged by said ratchet wrench for driving of the drive means, i.e. for release or tighten for example a screw or other fastener.

TECHNICAL BACKGROUND

Ratchet wrenches are used to turn a tool, screw or other component. This kind of hand tool is often used in mechanical engineering, in different environments and hence there are many different developed ratchet wrenches. Usually a ratchet wrench is equipped with some kind of lever for change of the rotational direction, this makes the tool complex and requests many parts.

There are a number of different ratchet wrenches on the market, generally they are difficult to dismount and/or comprises many parts, complex design or long narrow bore, which make washing/cleaning/sterilization time consuming or more even impossible. Washing/cleaning/sterilization is important for the function of a tool, but also of great importance when used in a clean environment, for example at surgery when a tool is used in an sensitive environment.

For example the tool described in US 2005/0268751 is not designed for disassembly and has further a number of narrow gaps and lose parts which makes cleaning very difficult.

Also the ratchet wrench described in GB 250127 is difficult to clean since it is designed with for example a fixed joint.

Both tools described in the documents mentioned above (US 2005/0268751, GB 250127) are dependent on the friction for their operation.

SUMMARY OF THE INVENTION

One object of the present invention is to provide a device with few parts which is easy to disassemble and easy to wash, sterilize or disinfect.

A further object of the present invention is to facilitate and make the handling of the tool more efficient for the user, like for example dental or surgery personnel.

At least one of these objects can be achieved by a ratchet wrench comprising a head having a driving aperture for engaging a drive means rotatable therein, a handle mounted for tilting movement in relation to said head. Provided is a first state where the drive means is allowed to freely rotate and a second state where said drive means is engaged by said ratchet wrench for driving of the drive means. Further the handle is movable, into and out from a mounting position, in the longitudinally direction of the handle.

The driving aperture with driving means is provided for transmitting a torque from the handle to a tool or other mechanical component. Further the head is acting as a housing for holding/supporting the handle and driving means.

The first and second state provided by the tilting handle will provide a simple and efficient way of operating the ratchet wrench. This is since the geometry will cause the handle to tilt when it is moved towards the first state where the handle is out of engagement from the driving means. Consequently, when the handle is moved in the opposite direction the head and handle will be aligned and operate the driving means to rotate.

The driving means, head and handle are designed for quick and simple disassembling, which provides improvements to the user compared to prior art when it comes to time efficiency, cleaning and handling.

It may be valuable if the head has an aperture positioned on the opposite side of said driving aperture in relation to the mounted position of the handle, for longitudinal movement of the handle through said aperture. In this way it is easy to mount the handle to the head by inserting the distal end of the handle through the disassembly aperture of the head and further moving the entire length of the handle through the head to a mounted position with the adjacent end of the handle in position inside the head. When the driving means is introduced in the driving aperture it will prevent the handle from coming loose from the head. Hence, the handle and head are safely mounted together in a simple way.

An advantage may be gained if said head has a retaining stop for the handle in the longitudinal direction. This will keep the handle and head together in the mounted position due to geometrical locking. The retaining stop can be formed as a protruding part or other geometry interacting with the head for interconnection.

It may be advantageous if the handle has an integrated spring means interacting with said head in the assembled position of said ratchet wrench. If the spring means is integrated with the handle there will be no extra or loose part that, for example, can be lost.

Advantageously, said spring means is interacting with the head both in longitudinal and tilting direction of the handle. The spring means is consequently used to create a transversal and longitudinal force between the handle and head. Where the transversal force acts to return the handle and head to an aligned position, i.e. the second state. The longitudinal force will both keep the handle and head in the desired internal mounting position during assembling and also act between the handle and head during the tilting movement of the handle.

Preferably said handle having an engagement portion for driving engagement with the driving means in said second state. The driving means is provided with a number of circumferentially positioned recesses for engagement with the engagement portion of the handle. In this way the "ratch" effect will be provided between the engagement portion which is forced towards the recesses by the spring. The engagement portion is formed with respect to the geometrical interaction between head and handle.

It may be advantageous if the handle has a protuberance interacting with said retaining stop of the head for providing said tilting movement between the handle and the head. This interaction between the protuberance and the stop will cause the handle and head to remain interconnected. The interacting stop and protuberance are preferably formed with a non complex geometry, but any suitably geometry or component can be used for this interaction.

Preferably the ratchet wrench according to the invention is provided with a cylindrical pin constituting retaining stop and recess surface.

Further the head is provided with at least three through bores, for the handle, driving means and pin respectively, which provides a non complicated and efficient manufacturing of the head.

Preferably the spring means is constituted of a strip of spring steel material, which is easily attached to the handle.

Such a ratchet wrench is well suited for environments with high demand of cleanness for example surgery or implanting of dental implant components or the like. Furthermore, the ratchet wrench is admitting an easy disassembly with few parts that can be washed or sterilized with a good result in a washing machine, autoclave or the like.

BRIEF DESCRIPTION OF DRAWINGS

By way of example, currently preferred embodiments of the present invention will now be described with reference to the accompanying figure of drawing in which;

FIG. 2a-d shows in perspective views a sequence of assembling of the ratchet wrench according to the invention.

FIG. 3a shows a sectional view of the ratchet wrench in the second engaged state.

FIG. 3b shows a sectional view of the ratchet wrench in the first state.

FIG. 4a shows a sectional view of an alternative embodiment of the ratchet wrench in the second state.

FIG. 4b shows a sectional view of an alternative embodiment of the ratchet wrench in the first state.

FIG. 5a shows a top view of further an alternative embodiment of the ratchet wrench in the first state.

FIG. 5b shows a top view of further an alternative embodiment of the ratchet wrench in the second state.

DESCRIPTION OF PREFERRED EMBODIMENTS

Figure 1:
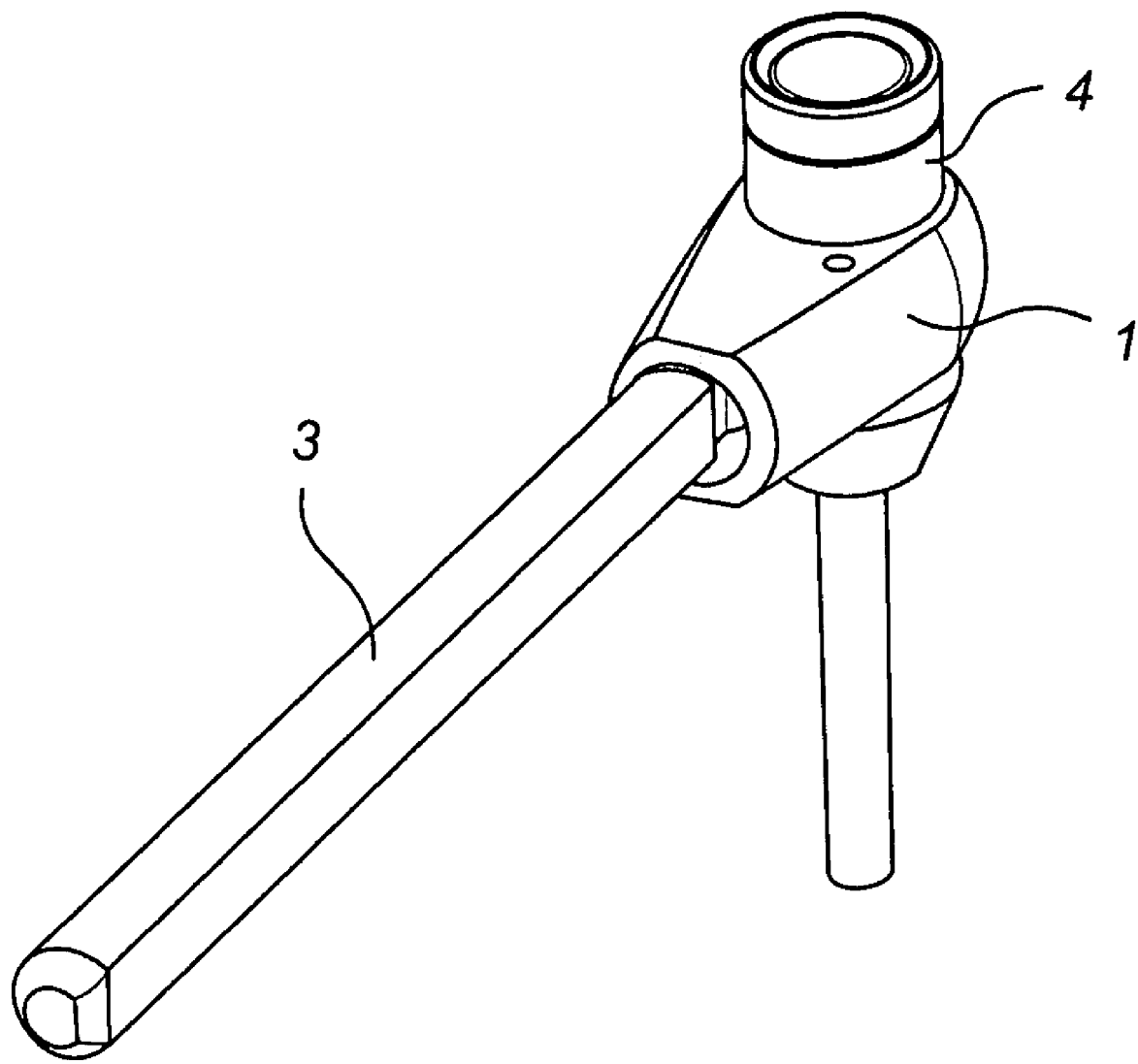
FIG. 1 discloses perspective view of a ratchet wrench engaged with drive means.

FIG. 1 shows a ratchet wrench according to the invention in an assembled condition with the handle 3 interconnected with the head 1, a driving means 4 is inserted in the driving aperture 2 of the head 1.

Figure 2A:
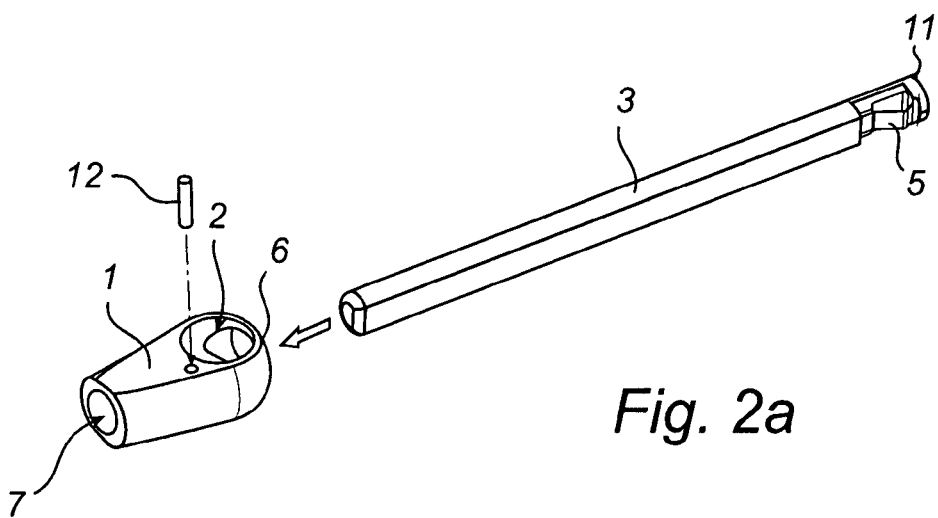

FIG. 2a describes how assembling of the ratchet wrench is performed by inserting the distal end of the handle 3 through the disassembly aperture 6 of the head. The elongated handle 3 is moved in the longitudinal direction through the disassembly aperture 6 and further through the opposite aperture 7 of the head 1 to an assembly position shown in FIG. 2b. The handle 3 will stop with its protuberance 10 against the retaining stop/surface 8 of the pin mounted in the head, as shown in FIG. 3a. During this assembling the spring 5 will be bent towards the handle by the pin 12 when the handle is moved in the longitudinal direction, the spring 5 will pass the retaining stop/surface 8 of the pin 12 to reach the assembled position with the spring 5 in its resting position in contact with the pin 12. During this movement and bending of the spring 5, the spring will be compressed towards the handle 3 when passing the pin 12. It is also possible to design the head with retaining stop and recess, corresponding to the stop and recess surfaces 8, 9 of the pin, as shown in FIG. 4a and 4b, for interaction with the spring 5 and handle 3. In the preferred embodiment both the retaining stop surface 8 and the recess surface 9 are constituted of two surfaces of the pin 12, i.e. the surfaces directed in the longitudinal direction of the handle. This design provides a cheap and simplified manufacturing.

Further the spring 5 is formed with a bent shape, with two bendings for interaction with the head 1, and to fit with the shape of the handle, the bent shape will further facilitate the spring 5 to be compressed/bent when the spring 5 is slid passing the pin 12. The angled surface of the spring 5 will further facilitate the spring 5 to interact with the pin 12 to create a longitudinal force between the head 1 and handle 3.

Figure 2B:
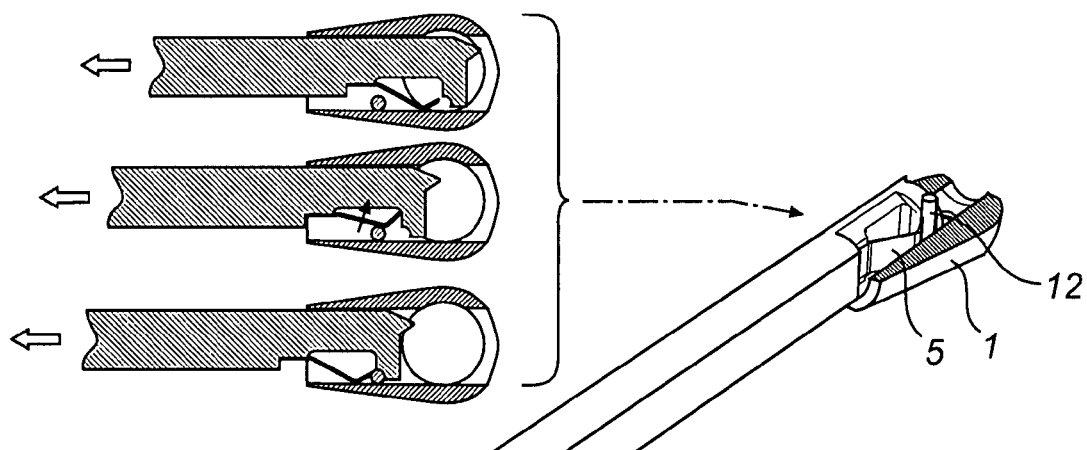
Figure 2C:
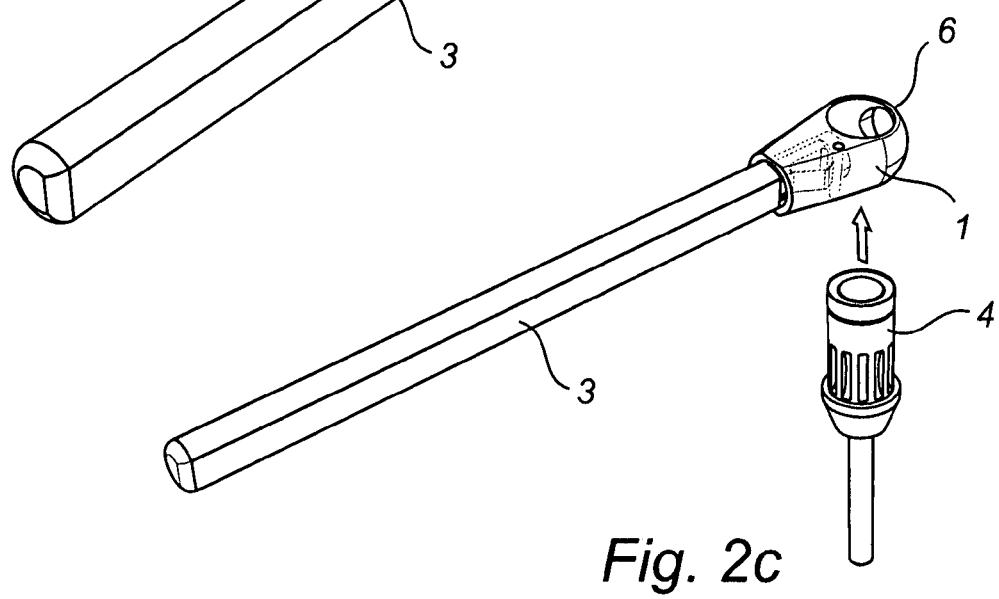

In FIG. 2b-2c is shown how the driving means 4 is inserted perpendicular into the driving aperture 2 of the head 1. To facilitate this insertion the engagement portion 11 of the handle is chamfered for smooth engagement with the recesses of the driving means 4. When the driving means 4 is in its assembled position (FIG. 2c) it will prevent the handle 3 from coming loose from the head 1 since the driving means 4 is blocking the handle from access to the disassembly aperture 6.

The driving means 4 is provided with circumferentially oriented recesses for engagement with the engagement portion 11 of the handle 3. The driving means 4 will be kept in its mounted position, in the driving aperture 2, due to the engagement between the engaging portion 11 of the handle 1 and the circumferentially oriented recesses of the driving means 4.

Further the handle and head is prevented from an incorrect mounting due to the geometry of the head and the apertures 6, 7 in combination with the geometry of the protuberance 10 of the handle, for example this can be achieved by asymmetric geometries or in other suitable ways.

In brief the assembling/disassembling of the ratchet wrench can be performed without any tools. It consist of only two main parts (handle and head) this facilitates sterilization and cleaning. Further the driving means is connectable to the ratchet wrench forming a third part that can be considered as a part of the ratchet wrench alternatively as a part of the component to which the torque is applied. However the driving means is provided for connecting the ratchet wrench and the component to be operated and transmit torque to this component.

In FIG. 3a the handle 3 is shown in the engaged position with the driving means 4. When the handle 3 is moved in a clockwise direction the ratchet wrench will transfer a torque via the driving means 4 to a tool, fastening component or another component attached to the driving means 4. The handle 3 is aligned with the head 1 and supported by the inner wall of the aperture 7, further the protuberance 10 will interact with the pin 12 or retaining stop 8 and hence the engagement portion 11 will remain engaged with the a recess of the driving means 4. Consequently the ratchet wrench will transmit torque due to this geometrical "locking" between handle and head, when the handle is moved clockwise. If the user need to transmit a torque in the counter clockwise direction the ratchet wrench has to be turned up side down, i.e. inserting the driving means 4 from the opposite side of the driving aperture 6 compared to what is shown in for example FIG. 2b.

In FIG. 3b is shown the ratcheting position of the handle. When the handle 3 is moved counter clockwise (in FIG. 3b) the ratchet wrench will not transmit any torque and, as mentioned above, this ratcheting will occur at clockwise movement if the ratchet wrench is turned up side down, i.e. the driving means 4, is inserted from the opposite side of the driving aperture 2.

When the handle is moved counter clockwise, as shown in FIG. 3b, the spring 5 is set to act and the handle 3 will tilt relatively to the head 1. Since the spring 5 acts both in the tilting/rotational direction and the longitudinal direction the handle and head will be kept in contact with the protuberance 10 against the pin 12 or retaining stop 8. Consequently the head and handle will tilt relatively each other around a pivot axis of the pin 12, whereupon the engaging portion 11 will come out of engagement from the driving means 4 and the ratchet wrench will not transmit driving torque to the driving means 4. The spring 5 will try to return the handle and the engagement portion 11 into each recess of the driving means 4 and hence there will be a ratcheting sound when the engagement portion 11 passes the recesses of the driving means 4. If the counter clockwise movement (FIG. 3*b*) is interrupted the ratchet wrench will immediately be ready for transmitting a torque to the driving means if the handle 3 is operated in the opposite direction. This is since the spring 5 will return the engagement portion 11 into a recess of the driving means 4 and geometrically interlock the ratchet wrench with the driving means 4.

The handle 3 is preferably elongated for providing a means for manually applying a desirable torque, but an elongated form does also provide remote access to the driving means 4. The driving means 4 can be provided with a male or female connection for a tool or other component (not shown), this male or female connection can be performed as a square, hexagonal or other shape suitable for transmitting a torque.

The handle 3 is manufactured from an elongated steel profile, the protuberance 10 is formed by machining of the entire length of the handle, leaving material in the end forming the protuberance 10. Further the recesses in the handle for the spring 5 is also machined, e.g. by milling, like the engagement portion 11. The spring 5 is attached to the handle 3 by a screw, welding, soldering, by using an adhesive or other suitable method. The spring 5 is preferably a plate spring, but can also be a wire spring as shown in FIG. 4*a* and 4*b*. The pin 12 is attached to the head 1 by press mounting it in the prepared hole. The use of the pin enable a simple machining for manufacturing of the head, the cavities can be made by drilling operations.

In an alternative embodiment (not shown) the head is, in the assembled condition, prevented from being moved of the distal end of the handle, for example due to a scale or other device mounted on the handle acting as an obstacle. Such an embodiment will prevent head and handle to be lost from each other. Further it would be possible to provide a cleaning position for the head, i.e. where the head is moved along the handle to a position between the distal and adjacent end respectively. In this position it would be possible to access the adjacent end of the handle for cleaning.

In further an alternative embodiment the spring 5' is constituted of an o-ring which is attached around the handle 3' and around a portion of the head 1' as shown in FIG. 5*a* and 5*b*. In this embodiment the head 1' is provided with a sloping surface, which is interacting with protrusions of the adjacent end of the handle 3'. These protrusions are provided in a perpendicular direction compared to the protuberance 10 shown in FIG. 3*a*-*b*.

In a further alternative embodiment, not shown, the spring is integrated in the head. In another embodiment the handle is mounted direct with the adjacent end of the handle into the head, for example by a bayonet coupling (not shown) or the like.

As mentioned above it is obvious that the effect from for example a clockwise rotation will be the opposite if the ratchet wrench is mounted up side down on the driving means, i.e. the effect will instead be as for a counter clockwise rotation.

The invention claimed is:

1. A ratchet wrench comprising;
    a head having a driving aperture for engaging a drive means rotatable therein;
    a handle mounted for tilting movement in relation to said head, providing a first state where the drive means is allowed to freely rotate and a second state where said drive means is engaged by said ratchet wrench for driving of the drive means,
    wherein said handle is movable, into and out from a mounting position in a longitudinal direction of the handle, whereby one end of said handle is moveable through a first aperture and further through a second aperture of the head, said first and second apertures extending laterally relative a longitudinal axis of the driving aperture.

2. The ratchet wrench according to claim 1, wherein said head has a retaining stop for said handle in the longitudinal direction.

3. The ratchet wrench according to claim 2, wherein said handle has a protuberance interacting with said retaining stop of the head for providing said tilting movement between the handle and the head.

4. The ratchet wrench according to claim 3, wherein a cylindrical pin is provided as the retaining stop.

5. The ratchet wrench according to claim 2, wherein a cylindrical pin is provided as the retaining stop.

6. The ratchet wrench according to claim 2, wherein said handle has an integrated spring means interacting with said head in the assembled position of said ratchet wrench.

7. The ratchet wrench according to claim 2, wherein said handle has an engagement portion for driving engagement with the driving means in said second state.

8. The ratchet wrench according to claim 1, wherein said handle has an integrated spring means interacting with said head in the assembled position of said ratchet wrench.

9. The ratchet wrench according to claim 8, wherein said spring means interacts with the head both in the longitudinal and a tilting direction of the handle.

10. The ratchet wrench according to claim 9, wherein said handle has an engagement portion for driving engagement with the driving means in said second state.

11. The ratchet wrench according to claim 9, wherein said handle has a protuberance interacting with said retaining stop of the head for providing said tilting movement between the handle and the head.

12. The ratchet wrench according to claim 9, wherein a cylindrical pin is provided as the retaining stop.

13. The ratchet wrench according to claim 8, wherein said spring means is constituted of a strip of spring steel material.

14. The ratchet wrench according to claim 8, wherein said handle has an engagement portion for driving engagement with the driving means in said second state.

15. The ratchet wrench according to claim 8, wherein said handle has a protuberance interacting with said retaining stop of the head for providing said tilting movement between the handle and the head.

16. The ratchet wrench according to claim 8, wherein a cylindrical pin is provided as the retaining stop.

17. The ratchet wrench according to claim 1, wherein said handle has an engagement portion for driving engagement with the driving means in said second state.

18. The ratchet wrench according to claim 17, wherein said handle has a protuberance interacting with said retaining stop of the head for providing said tilting movement between the handle and the head.

19. The ratchet wrench according to claim 17, wherein a cylindrical pin is provided as the retaining stop.

20. The ratchet wrench according to claim 1, wherein the head is provided with at least three through bores, for the handle, the driving means and a pin, respectively.

* * * * *